United States Patent
Blackwell, Jr. et al.

(10) Patent No.: US 9,235,617 B1
(45) Date of Patent: Jan. 12, 2016

(54) SECURING DATE DATA FIELDS

(71) Applicant: ALLSCRIPTS SOFTWARE, LLC, Chicago, IL (US)

(72) Inventors: Gordon Lyles Blackwell, Jr., Raleigh, NC (US); Brent Arasimowicz, Auburn, NH (US)

(73) Assignee: ALLSCRIPTS SOFTWARE, LLC, Chicago, IL (US)

( * ) Notice: Subject to any disclaimer, the term of this patent is extended or adjusted under 35 U.S.C. 154(b) by 157 days.

(21) Appl. No.: 13/972,711

(22) Filed: Aug. 21, 2013

(51) Int. Cl.
*G06F 17/30* (2006.01)

(52) U.S. Cl.
CPC ............................. *G06F 17/30424* (2013.01)

(58) Field of Classification Search
CPC ............ G06F 17/30424; G06F 19/322; G06F 21/6245; G06F 19/328; G06F 21/6227; G06F 21/60; G06F 21/88; G06Q 50/24

USPC ........................................................ 707/769
See application file for complete search history.

(56) References Cited

U.S. PATENT DOCUMENTS

| | | | | |
|---|---|---|---|---|
| 7,668,820 B2 * | 2/2010 | Zuleba | ........................ | 707/765 |
| 7,877,398 B2 * | 1/2011 | Kroeschel et al. | ............. | 707/757 |
| 8,275,850 B2 * | 9/2012 | Kohan et al. | .................. | 709/212 |
| 8,924,401 B2 * | 12/2014 | Raj et al. | ....................... | 707/757 |

* cited by examiner

*Primary Examiner* — Sheree Brown
(74) *Attorney, Agent, or Firm* — Tillman Wright, PLLC; Chad D. Tillman; Jeremy C. Doerre

(57) ABSTRACT

A method facilitating searching of data containing protected date information includes generating one or more randomly escalating dateID values for each date during a time period and storing such generated dateID values in a lookup table together with an encrypted, associated date value. Such generated dateID values can be stored in a datasource in place of protected dates in order to safeguard protected health information. In one or more preferred implementations, a de-identified date is stored in the lookup table in association with a dateID, and utilized for searching operations.

19 Claims, 11 Drawing Sheets

| Service Dates | # Records | Conventional Time (ms) | DateID Lookup (ms) |
|---|---|---|---|
| 01/01/1900 – 12/31/1900 | 0 | 21,868 | 673 |
| 01/01/1997 – 12/31/1997 | 43,026 | 18,826 | 741 |
| 01/01/2005 – 12/31/2005 | 82,540 | 15,808 | 840 |
| 01/01/2012 – 12/31/2012 | 127,248 | 12,796 | 850 |
| Average Time | | 17,325 | 776 |

*FIG. 6*

```
/****** Object: Table [dbo].[DateIDs_Test] Script Date: 5/21/2013 1:56:42 PM ******/
CREATE TABLE [dbo].[DateIDs](
    [DateID] [int] NOT NULL,
    [LookupDate] [date] NOT NULL,
CONSTRAINT [PK_Dates] PRIMARY KEY CLUSTERED
(
    [DateID] ASC
)WITH (PAD_INDEX = OFF, STATISTICS_NORECOMPUTE = OFF, IGNORE_DUP_KEY = OFF, ALLOW_ROW_LOCKS = ON, ALLOW_PAGE_LOCKS = ON) ON [PRIMARY]
) ON [PRIMARY]

/****** Object: Table [dbo].[DateIDs_Test] Script Date: 5/21/2013 2:07:10 PM ******/
CREATE TABLE [dbo].[DateIDs_Test](
    [DateID] [int] IDENTITY(1,1) NOT NULL,
    [LookupDate] [varbinary](128) NOT NULL,
    [UnEncryptDate] [datetime] NOT NULL,
    [LookupID] [int] NOT NULL,
    [Notes] [varchar](500) NOT NULL,
CONSTRAINT [PK_DateIDs_Test] PRIMARY KEY CLUSTERED
(
    [DateID] ASC
)WITH (PAD_INDEX = OFF, STATISTICS_NORECOMPUTE = OFF, IGNORE_DUP_KEY = OFF, ALLOW_ROW_LOCKS = ON, ALLOW_PAGE_LOCKS = ON, FILLFACTOR = 90) ON [PRIMARY]
) ON [PRIMARY]

```
/****** Object: StoredProcedure [dbo].[InsertDateIDs]   Script Date: 5/21/2013 9:02:26 AM ******/
-- =============================================
-- Author:      Blackwell, Gordon
-- Create date: May 20, 2013
-- Description:
-- =============================================
CREATE PROCEDURE [dbo].[InsertDateIDs]
AS
BEGIN
    DECLARE @idPtr INT
    DECLARE @datePtr DATE
    DECLARE @lastDatePtr DATE
    DECLARE @randomNum INT
    DECLARE @randLower INT
    DECLARE @randUpper INT
    DECLARE @random INT
    DECLARE @lastYearStart INT
    DECLARE @idsPerDate INT
    DECLARE @idLoopPtr INT
    DECLARE @exists INT
    DECLARE @minID INT
    DECLARE @dayOfYear INT
    DELETE
    FROM Dates
    SET @idsPerDate = 3      -- Each day of the year may have multiple related IDs /
                                Additional IDs reduces the probability of relating ID to a given date
    SET @datePtr = '01/01/1850'   -- Starting date
    SET @lastDatePtr = '12/31/2015'  -- Last date to assign
    SET @randLower = 1       -- The minimum allowed value that the random generator is allowed
    SET @randUpper = 99      -- The maximum allowed value that the random generator is allowed
    SET @idPtr = 0           -- The variable used to assign to each day
    SET @dayOfYear = 1       -- A numeric value that represents the current day of the year
    SET @minID = 0           -- The minimum value that the ID can be assigned
                                (cannot be < the ID of the prior day or same day of the prior year)
...
```

FIG. 8A

```
...
-- Loop to include all requested dates
WHILE @datePtr <= @lastDatePtr
BEGIN SET @idLoopPtr = 1
    -- Loop to insert the required number of IDs per day
    WHILE @idLoopPtr <= @idsPerDate
    BEGIN
        -- Capture the current day of the year (a value between 1-365)
        SET @dayOfYear = datepart(dy,@datePtr)
        -- Store a random number
        SET @random = ROUND(((@randUpper - @randLower -1) * RAND() + @randLower), 0)
        -- The ID equals a random amount greater than the minimum value
        SET @idPtr = @idPtr + @random
        -- The following loop verifies that an ID is unique
        SET @exists = 1
        WHILE @exists > 0
        BEGIN
            SET @exists = 0
            -- @exists will continue to equal 0 if the ID has not been used
            SELECT @exists = ISNULL(DateID, 0)
            FROM Dates
            WHERE DateID = @idPtr
            -- Skip that ID if it has already been used
            IF @exists > 0
                SET @idPtr = @idPtr + 1
        END
        -- Insert the ID for the Date
        INSERT INTO Dates(DateID, LookupDate) VALUES (@idPtr, @datePtr)
        SET @idLoopPtr = @idLoopPtr + 1
    END
    -- Move to the next day
    SET @datePtr = DATEADD(d, 1, @datePtr)
END
```

*FIG. 8B*

```
/****** Object:  StoredProcedure [dbo].[GetDateIDForDate]    Script Date: 6/14/2013 1:52:30 PM ******/
CREATE PROCEDURE [dbo].[GetDateIDForDate]
(
    @LookupDate DATE,
    @DeIDOffset INT = 15
)
AS
BEGIN
    DECLARE @dates TABLE (ID INTEGER IDENTITY(1,1), DateID INT, LookupDate DATE)
    DECLARE @random INT
    DECLARE @count INT
    DECLARE @min INT
    DECLARE @max INT
    OPEN SYMMETRIC KEY DateID_Key DECRYPTION BY CERTIFICATE DateID_Cert;
    INSERT INTO @dates(DateID, Lookupdate)
        SELECT DateID, CONVERT(DATE, CONVERT(VARCHAR(50), DECRYPTBYKEY(LookupDate)))
        FROM DateIDs
        WHERE DeIdentifiedDate BETWEEN DATEADD(d, -@DeIDOffset, @LookupDate)
                                  AND DATEADD(d,  @DeIDOffset, @LookupDate)
    DELETE
    FROM @dates
    WHERE Lookupdate != @LookupDate
    SELECT  @count = COUNT(*),
            @min = MIN(ID),
            @max = MAX(ID)
    FROM @dates
    SET @random = @min + ROUND(@count * RAND(), 0)
    SET @random = IIF( @random > @max, @max, @random)
    SELECT DateID
    FROM @dates
    WHERE ID = @random
END
```

FIG. 9

```
/****** Object: StoredProcedure [dbo].[GetStartEnd] Script Date: 6/14/2013 2:00:09 PM ******/
CREATE PROCEDURE [dbo].[GetStartEndDateIDs]
(
    @LookupDate DATE,
    @DeIDOffset INT = 15
)
AS
BEGIN
    DECLARE @dates TABLE (DateID INT, LookupDate DATE, LowHighFlag VARCHAR(50))
    DECLARE @FromDate INT
    DECLARE @ToDate INT
    OPEN SYMMETRIC KEY DateID_Key
    DECRYPTION BY CERTIFICATE DateID_Cert;
    INSERT INTO @dates(DateID, Lookupdate, LowHighFlag)
        SELECT    DateID, CONVERT(DATE, CONVERT(VARCHAR(50), DECRYPTBYKEY(LookupDate))),
                DECRYPTBYKEY(LowHighFlag, 1, HashBytes('SHA1', CONVERT(varbinary, DateID)))
        FROM    DateIDs
        WHERE    DeIdentifiedDate BETWEEN DATEADD(d, -@DeIDOffset, @LookupDate)
                                AND DATEADD(d, @DeIDOffset, @LookupDate)

DELETE
    FROM @dates
    WHERE Lookupdate != @LookupDate
    SELECT @FromDate = DateID
    FROM @dates
    WHERE LookupDate = @LookupDate
        AND LowHighFlag='L'
    SELECT @ToDate = DateID
    FROM @dates
    WHERE LookupDate = @LookupDate
        AND LowHighFlag='H'
    SELECT @FromDate AS FromDate, @ToDate AS ToDate
END
```

*FIG. 10*

… # SECURING DATE DATA FIELDS

COPYRIGHT STATEMENT

All of the material in this patent document is subject to copyright protection under the copyright laws of the United States and other countries. The copyright owner has no objection to the facsimile reproduction by anyone of the patent document or the patent disclosure, as it appears in official governmental records but, otherwise, all other copyright rights whatsoever are reserved.

BACKGROUND OF THE INVENTION

The present invention generally relates to securing protected data, such as protected health information.

The Health Insurance Portability and Accountability Act (HIPAA) characterizes data that may identify an individual as protected health information (PHI). Dates such as a birthdate or a patient encounter date represent PHI and must be secured when stored, e.g. in a database. Storing data in a noncompliant (e.g. unsecured) manner could result in sizable penalty fees.

One common approach to securing PHI data is encryption. Encrypted data is generally recognized as secured when it can, for example, only be deciphered using complex mathematical algorithms and a predetermined key.

While encrypting PHI data satisfies HIPAA regulations, this approach, and in particular the eventually required decryption, can significantly impact system performance. The most significant impact occurs when encrypted data is required for a search or sort routine. The degraded results generally occur because a database system cannot leverage indexes of encrypted fields. As a result, the system must decrypt each record as it performs a full table scan, e.g. the system must decrypt and review every record, which is typically an extremely time consuming process.

Needs exists for improvement in securing protected data. These and other needs are addressed by one or more aspects of the present invention.

SUMMARY OF THE INVENTION

The present invention includes many aspects and features. Moreover, while many aspects and features relate to, and are described in, the context of protected health information, the present invention is not limited to use only in this context, as will become apparent from the following summaries and detailed descriptions of aspects, features, and one or more embodiments of the present invention.

Accordingly, one aspect of the present invention relates to a method for searching of data containing protected date information representing protected health information, the method comprising adding dateID and date values to a lookup table by, for a start date, adding a first dateID and date value pair to the lookup table by generating a first random number, adding the generated first random number to a minimum value to establish a first ID value, determining whether the established first ID value is unique, and incrementing the established first ID value if it is not until it is unique, thereafter, once it is determined that the established first ID value is unique, inserting the established first ID value in association with the start date into the lookup table; for the start date, adding an additional number of dateID and date value pairs based on an indication of a desired number of dateIDs to be assigned to a date by repeatedly generating a respective random number, adding the generated respective random number to the established first ID value to establish a respective ID value, determining whether the established respective ID value is unique, and incrementing the established respective ID value if it is not until it is unique, thereafter, once it is determined that the established respective ID value is unique, inserting the established respective ID value in association with the start date into the lookup table; for each respective date between the start date and an end date, adding a number of dateID and date value pairs, the number being based on an indication of a desired number of dateIDs to be assigned to a date, by repeatedly generating a respective random number, adding the generated respective random number to the last established ID value to establish a current respective ID value, determining whether the established current respective ID value is unique, and incrementing the established current respective ID value if it is not until it is unique, thereafter, once it is determined that the established current respective ID value is unique, inserting the established current respective ID value in association with the respective date into the lookup table. The method further includes receiving, from a user via an input device, a query for records falling within a certain date range, and determining a minimum dateID value corresponding to a query start date associated with the certain date range by inserting, into a first dummy table, records from the lookup table that have a de-identified date value falling within a certain number of days of the query start date, deleting, from the first dummy table, one or more records where a decrypted date value of the record does not correspond to the query start date, and determining a minimum dateID value of the remaining records. The method still further includes determining a maximum dateID value corresponding to a query end date associated with the certain date range by inserting, into a second dummy table, records from the lookup table that have a de-identified date value falling within a certain number of days of the query start date, deleting, from the second dummy table, one or more records where a decrypted date value of the record does not correspond to the query end date, and determining a maximum dateID value of the remaining records. The method further includes selecting, from a datasource containing records corresponding to patient encounters, all encounters having a dateID value falling within a range corresponding to the determined minimum and maximum dateID values, and presenting, to the user via a display device, an indication of one or more of the records selected from the datasource.

In a feature of one or more aspects, the first dummy table and the second dummy table are the same dummy table.

In a feature of one or more aspects, the first dummy table and the second dummy table are different dummy tables.

In a feature of one or more aspects, the datasource comprises a database.

In a feature of one or more aspects, the datasource comprises a data warehouse.

In a feature of one or more aspects, the datasource comprises a database of a data warehouse.

In a feature of one or more aspects, the method further includes generating a de-identified date for each dateID in the lookup table. In one or more implementations, the method further includes storing the generated de-identified date for each dateID in the lookup table in association with the respective dateID. In one or more implementations, each generated de-identified date is generated to be within a certain number of days of a date associated with the dateID the de-identified date is generated for. In one or more implementations, the certain number of days is fifteen days.

Another aspect relates to a method for facilitating searching of data containing protected date information representing protected health information, the method comprising adding dateID and date values to a lookup table by, for a start date, adding a first dateID and date value pair to the lookup table by generating a first random number, adding the generated first random number to a minimum value to establish a first ID value, determining whether the established first ID value is unique, and incrementing the established first ID value if it is not until it is unique, thereafter, once it is determined that the established first ID value is unique, inserting the established first ID value in association with the start date into the lookup table; for the start date, adding an additional number of dateID and date value pairs based on an indication of a desired number of dateIDs to be assigned to a date by repeatedly generating a respective random number, adding the generated respective random number to the established first ID value to establish a respective ID value, determining whether the established respective ID value is unique, and incrementing the established respective ID value if it is not until it is unique, thereafter, once it is determined that the established respective ID value is unique, inserting the established respective ID value in association with the start date into the lookup table; for each respective date between the start date and an end date, adding a number of dateID and date value pairs, the number being based on an indication of a desired number of dateIDs to be assigned to a date, by repeatedly generating a respective random number, adding the generated respective random number to the last established ID value to establish a current respective ID value, determining whether the established current respective ID value is unique, and incrementing the established current respective ID value if it is not until it is unique, thereafter, once it is determined that the established current respective ID value is unique, inserting the established current respective ID value in association with the respective date into the lookup table.

Another aspect relates to a method for searching of data containing protected date information representing protected health information utilizing a lookup table containing encrypted date values, dateID values, and de-identified date values. The method includes receiving, from a user via an input device, a query for medical records having a date value falling within a certain date range. The method further includes determining a minimum dateID value corresponding to a query start date associated with the certain date range by inserting, into a first dummy table, records from the lookup table that have a de-identified date value falling within a certain number of days of the query start date, and deleting, from the first dummy table, one or more records where a decrypted date value of the record does not correspond to the query start date, and determining a minimum dateID value of the remaining records. The method further includes determining a maximum dateID value corresponding to a query end date associated with the certain date range by inserting, into a second dummy table, records from the lookup table that have a de-identified date value falling within a certain number of days of the query start date, deleting, from the second dummy table, one or more records where a decrypted date value of the record does not correspond to the query end date, and determining a maximum dateID value of the remaining records. The method further includes selecting, from a datasource containing records corresponding to patient encounters, all encounters having a dateID value falling within a range corresponding to the determined minimum and maximum dateID values, and presenting, to the user via a display device, an indication of one or more of the records selected from the datasource.

In a feature of one or more aspects, the query for medical records comprises a query for patient encounter records.

In a feature of one or more aspects, the query for medical records comprises a query for patient procedure records.

In a feature of one or more aspects, the first dummy table and the second dummy table are the same dummy table.

In a feature of one or more aspects, the first dummy table and the second dummy table are different dummy tables.

In a feature of one or more aspects, the datasource comprises a database.

In a feature of one or more aspects, the datasource comprises a data warehouse.

In a feature of one or more aspects, the datasource comprises a database of a data warehouse.

In a feature of one or more aspects, inserting, into a second dummy table, records from the lookup table that have a de-identified date value falling within a certain number of days of the query start date comprises inserting records that have a de-identified date value falling within fifteen days of the query start date.

In a feature of one or more aspects, inserting, into a second dummy table, records from the lookup table that have a de-identified date value falling within a certain number of days of the query end date comprises inserting records that have a de-identified date value falling within fifteen days of the query end date.

In addition to the aforementioned aspects and features of the present invention, it should be noted that the present invention further encompasses the various possible combinations and subcombinations of such aspects and features. Thus, for example, any aspect may be combined with an aforementioned feature in accordance with the present invention without requiring any other aspect or feature.

BRIEF DESCRIPTION OF THE DRAWINGS

One or more preferred embodiments of the present invention now will be described in detail with reference to the accompanying drawings, wherein the same elements are referred to with the same reference numerals, and wherein.

FIG. 6 summarizes results of a comparison of a conventional methodology and an exemplary proof of concept implementation in accordance with one or more preferred embodiments; and FIGS. 7-10 illustrate code for the exemplary proof of concept implementation in accordance with one or more preferred embodiments.

DETAILED DESCRIPTION

Figure 1:
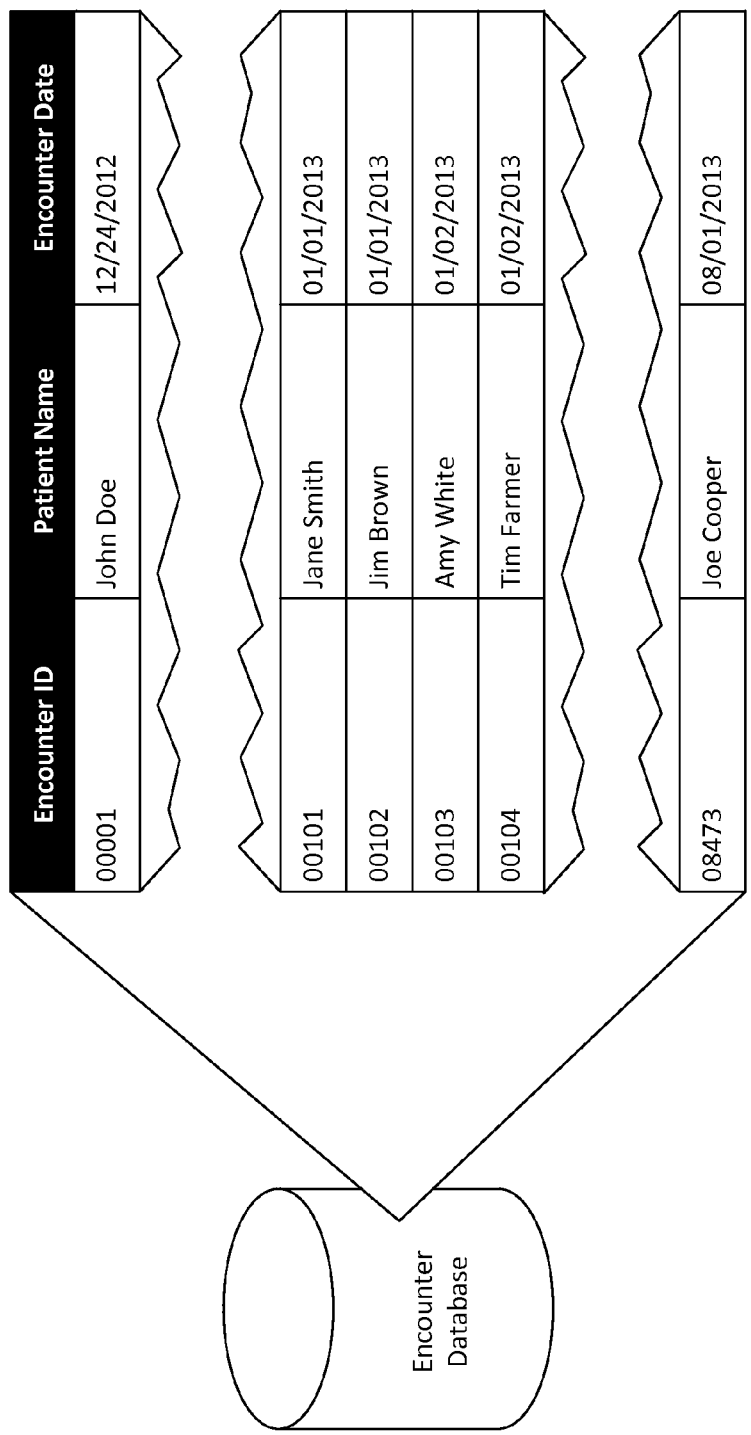
FIG. 1 illustrates an exemplary database storing information on patient encounters.

As a preliminary matter, it will readily be understood by one having ordinary skill in the relevant art ("Ordinary Artisan") that the present invention has broad utility and application. As should be understood, any embodiment may incorporate only one or a plurality of the above-disclosed aspects of the invention and may further incorporate only one or a plurality of the above-disclosed features. Furthermore, any embodiment discussed and identified as being "preferred" is considered to be part of a best mode contemplated for carrying out the present invention. Other embodiments also may be discussed for additional illustrative purposes in providing a full and enabling disclosure of the present invention. As should be understood, any embodiment may incorporate only one or a plurality of the above-disclosed aspects of the invention and may further incorporate only one or a plurality of the above-disclosed features. Moreover, many embodiments, such as adaptations, variations, modifications, and equivalent arrangements, will be implicitly disclosed by the embodiments described herein and fall within the scope of the present invention.

Accordingly, while the present invention is described herein in detail in relation to one or more embodiments, it is to be understood that this disclosure is illustrative and exemplary of the present invention, and is made merely for the purposes of providing a full and enabling disclosure of the present invention. The detailed disclosure herein of one or more embodiments is not intended, nor is to be construed, to limit the scope of patent protection afforded the present invention, which scope is to be defined by the claims and the equivalents thereof. It is not intended that the scope of patent protection afforded the present invention be defined by reading into any claim a limitation found herein that does not explicitly appear in the claim itself.

Thus, for example, any sequence(s) and/or temporal order of steps of various processes or methods that are described herein are illustrative and not restrictive. Accordingly, it should be understood that, although steps of various processes or methods may be shown and described as being in a sequence or temporal order, the steps of any such processes or methods are not limited to being carried out in any particular sequence or order, absent an indication otherwise. Indeed, the steps in such processes or methods generally may be carried out in various different sequences and orders while still falling within the scope of the present invention. Accordingly, it is intended that the scope of patent protection afforded the present invention is to be defined by the appended claims rather than the description set forth herein.

Additionally, it is important to note that each term used herein refers to that which the Ordinary Artisan would understand such term to mean based on the contextual use of such term herein. To the extent that the meaning of a term used herein—as understood by the Ordinary Artisan based on the contextual use of such term—differs in any way from any particular dictionary definition of such term, it is intended that the meaning of the term as understood by the Ordinary Artisan should prevail.

Regarding applicability of 35 U.S.C. §112, ¶6, no claim element is intended to be read in accordance with this statutory provision unless the explicit phrase "means for" or "step for" is actually used in such claim element, whereupon this statutory provision is intended to apply in the interpretation of such claim element.

Furthermore, it is important to note that, as used herein, "a" and "an" each generally denotes "at least one," but does not exclude a plurality unless the contextual use dictates otherwise. Thus, reference to "a picnic basket having an apple" describes "a picnic basket having at least one apple" as well as "a picnic basket having apples." In contrast, reference to "a picnic basket having a single apple" describes "a picnic basket having only one apple."

When used herein to join a list of items, "or" denotes "at least one of the items," but does not exclude a plurality of items of the list. Thus, reference to "a picnic basket having cheese or crackers" describes "a picnic basket having cheese without crackers", "a picnic basket having crackers without cheese", and "a picnic basket having both cheese and crackers." Finally, when used herein to join a list of items, "and" denotes "all of the items of the list." Thus, reference to "a picnic basket having cheese and crackers" describes "a picnic basket having cheese, wherein the picnic basket further has crackers," as well as describes "a picnic basket having crackers, wherein the picnic basket further has cheese."

Referring now to the drawings, one or more preferred embodiments of the present invention are next described. The following description of one or more preferred embodiments is merely exemplary in nature and is in no way intended to limit the invention, its implementations, or uses.

FIG. 1 illustrates an exemplary database storing information on patient encounters. In this example, each encounter record includes, inter alia, an encounter ID, an identification of a patient (which may be a name or a patient ID), and an encounter date.

Figure 2:
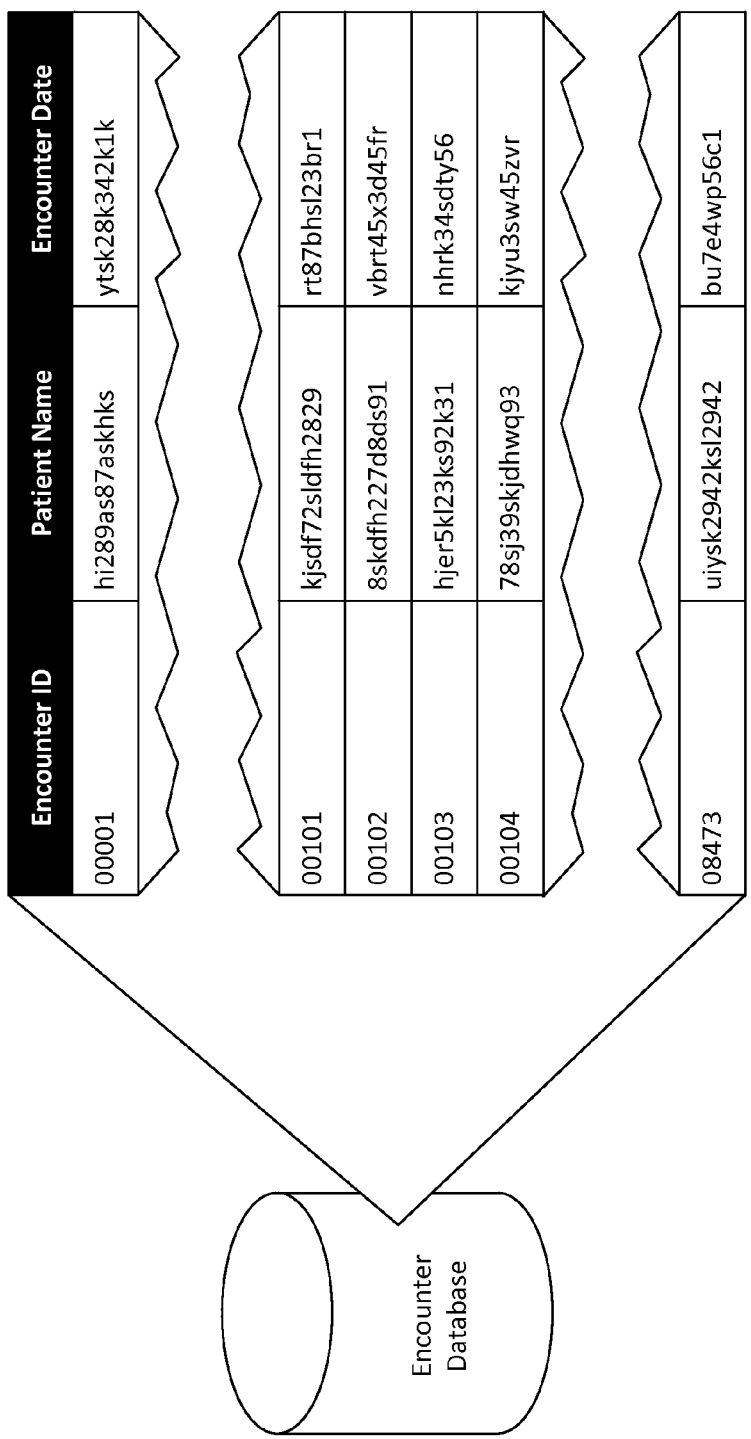
FIG. 2 illustrates an exemplary database in which a patient name and encounter date are encrypted.

It will be appreciated that this database includes information which could be characterized as protected health information (PHI) under HIPAA, and, accordingly, should be protected. As noted above, one common approach to securing PHI data is encryption. FIG. 2 illustrates encryption of the patient name and encounter date fields of each record. This approach, although HIPAA compliant, can significantly impact system performance. For example, if records need to be searched or sorted by encounter date, a decryption operation must be performed for each record as a full table scan is performed, which is typically an extremely time consuming process. Within a clinical data warehouse, an encounter date might represent a crucial conditional and sorting element, triggering a decryption process on billions of records prior to the compilation of several reports. Not only does this slow the response for a current user, but the excessive processing can contribute to growth of a "log-jam" as use requests begin to compete for system resources.

Figure 3:
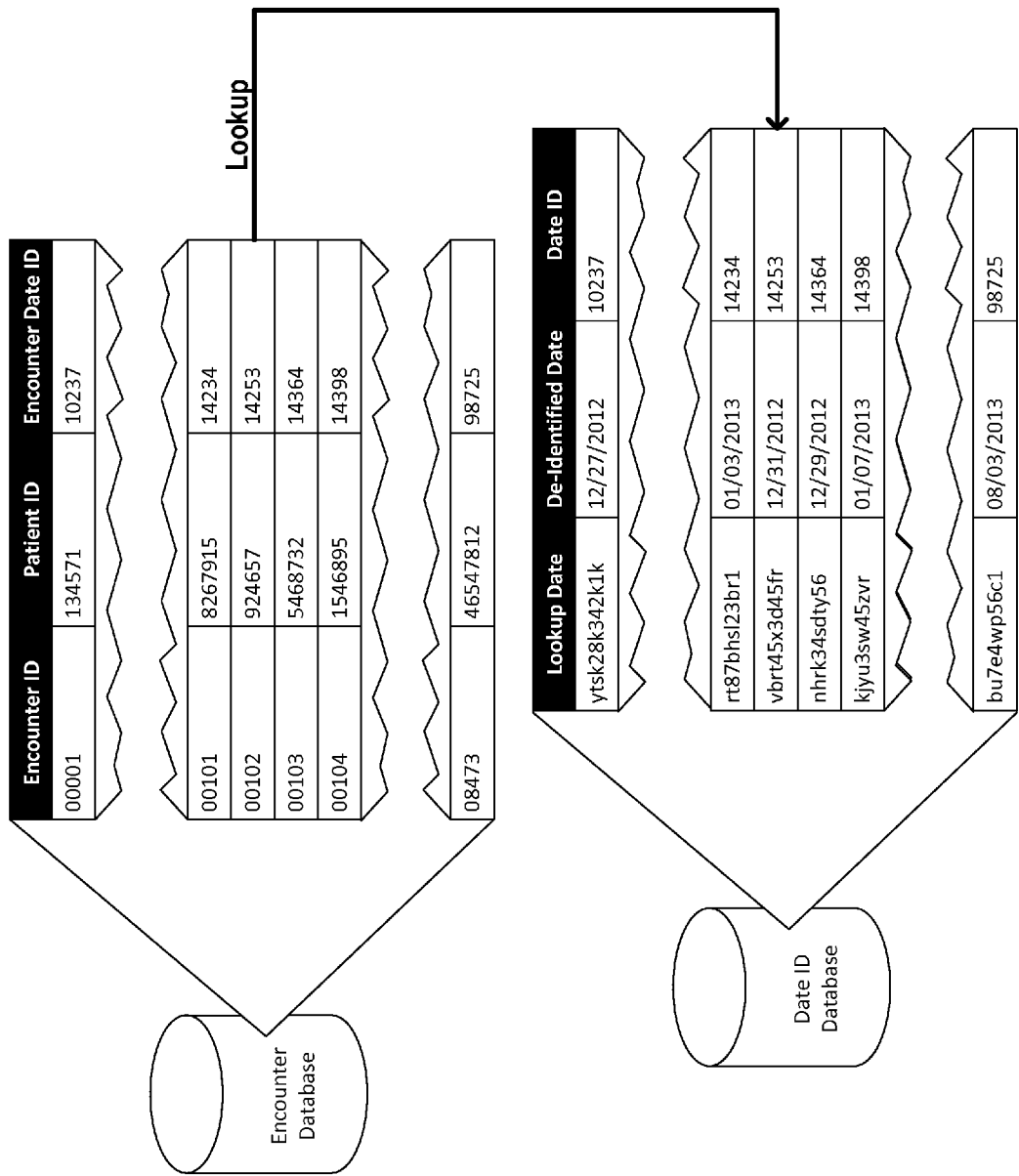
FIG. 3 illustrates use of a lookup table in accordance with one or more preferred embodiments.
Figure 4:
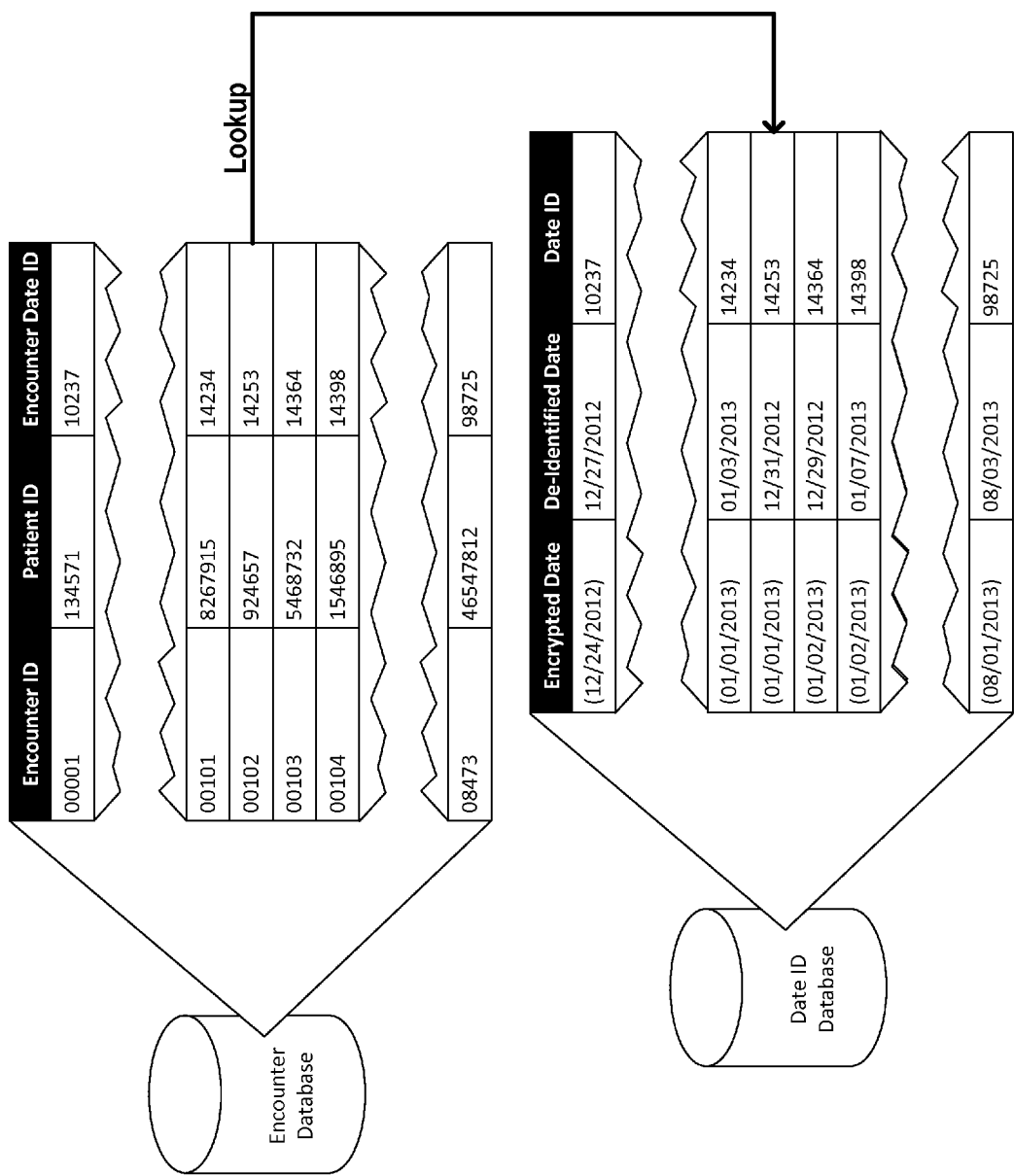
FIG. 4 illustrates the table of FIG. 3 with decrypted date values for illustrative purposes.
Figure 5:
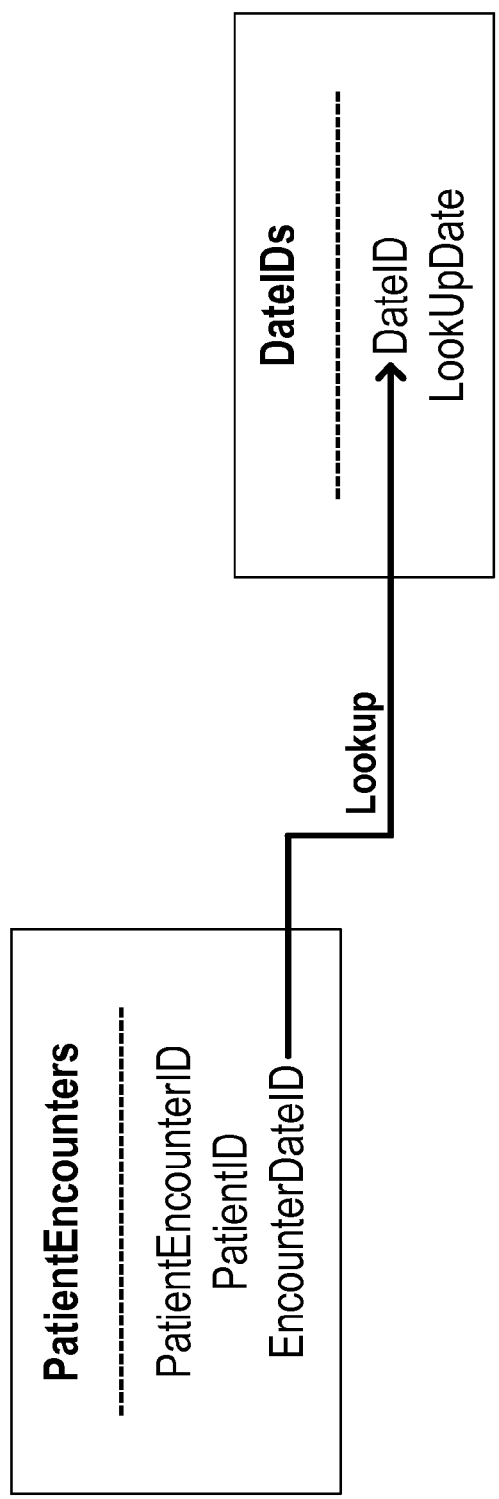
FIG. 5 schematically illustrates vis-à-vis exemplary data structures the lookup of a date based on a dateID associated with a patient encounter.

In a preferred methodology in accordance with one or more preferred implementations, rather than storing encrypted date values in an encounter database/table (or encrypting entire records therein), an unencrypted dateID value is stored which can be utilized to look up the actual date, as illustrated in FIG. 3. The actual date associated with a dateID is stored in a lookup table that is secured with encryption. Because significantly fewer records exist in the lookup table relative to the volume of patient records, processing time is dramatically reduced. FIGS. 3 and 4 illustrate use of the same lookup table, but FIG. 4 illustrates decrypted date values for purposes of illustration. FIG. 5 schematically illustrates vis-à-vis exemplary data structures the lookup of a date based on a dateID associated with a patient encounter.

In addition, in one or more preferred implementations, the lookup table further contains unencrypted de-identified dates that can be delivered when de-identified information is requested, as illustrated in FIG. 3, which can also speed up a dateID search. In one or more preferred implementations, such de-identified dates are configured to have a certain relationship to an actual date they correspond to, e.g. are configured to lie within a certain number of days, such as fifteen.

In preferred implementations, a date lookup table contains dates with a related dateID and de-identified date. Preferably, the dateID increases for each consecutive date, but the numeric value of the dateID follows a random progression pattern, as illustrated in FIG. 4.

In addition, a preferred methodology preferably allows for multiple dateIDs for each unique date, as also illustrated in FIG. 4. In one or more preferred implementations, the use of multiple dateIDs for a single date reduces risks for at least two reasons. First, the use of multiple dateIDs eliminates the ability for an authorized individual to relate dateIDs to dates based solely on patterns in the data. Second, if a dateID to date relationship is determined by an unauthorized individual, the number of records at risk of breach is reduced.

In a preferred implementation, twenty dateIDs are utilized for each date, but in various preferred implementations the number of DateIDs used to represent each date is not fixed, and, in fact, in one or more preferred implementations, the number of dateIDs utilized can be variable per date, e.g. Jan. 1, 2012 might have twenty dateIDs while Jan. 31, 2012 might only have fifteen.

In one or more preferred implementations, a methodology allows for the use of "false dates", e.g. date records that translate into completely erroneous values that can be used to obscure the start and end dates of a given interval of time.

In one or more preferred implementations, methodologies described herein are "feathered" into existing solutions that use relational databases without the need to incorporate proprietary add-ons or extensions. Various preferred implementations can be implemented on any SQL database platform.

In one or more preferred implementations, a system supports multiple, unique dateID lookup table instances. Further, various systems can each have their own unique lookup table instances. In one or more preferred implementations, access to one system or instance does not imply or suggest any greater advantage to breaching other systems or instances. Further, in one or more preferred implementations, if a need arises to create a new instance of a dateID table instance, e.g. because of a system breach, a new dateID instance can be readily created, mapped to the old dateID instance, and then the old instance can be completely retired without leaving any trace of the old table. This ability is inherent to one or more preferred implementations.

FIGS. 7-10 illustrate code for an exemplary proof of concept in accordance with one or more preferred embodiments. In an exemplary use case, the procedures of FIGS. 8A-10 were utilized in an exemplary proof of concept in conjunction with a datasource containing around seven million records. Queries were run on such datasource under two alternate methodologies. First, queries were run under a conventional methodology in which dates were stored utilizing encryption. Second, queries were run under a methodology in which dates were stored utilizing a dateID lookup table in accordance with the exemplary implementation associated with the code illustrated in FIGS. 8A-10.

FIG. 6 summarizes the results of this test. As illustrated in FIG. 6, the average query utilizing a dateID lookup table (as compared to a conventional methodology in which dates were stored utilizing encryption) was roughly twenty two times faster.

More specifically, FIGS. 8A-B illustrates an exemplary procedure for generating dateIDs for a lookup table. This process includes assigning, for each date from an initial start date to an end date, a certain number of dateIDs to each date. In the procedure defined in FIGS. 8A-B, this is accomplished by looping through the dates from the start date to the end date, and, for each date, capturing a current day of the year, generating a random number, and adding the random number to a minimum ID value (which cannot be less than an ID value for the previous day or the same day of the previous year), and verifying that the ID value is unique. If it is, then the ID value is inserted together with the date into the lookup table. If it is not, then the ID value is incremented until it is unique and then inserted together with the date into the lookup table. When the loop gets to the next date, the ID value used for the previous date is set as the minimum ID value, and a newly generated random number is added to such minimum ID value to arrive at a new ID value that is then tested for uniqueness.

FIGS. 9-10 illustrate exemplary procedures to be utilized in conjunction with a lookup table populated in accordance with the procedure of FIGS. 8A-B.

Specifically, FIG. 9 illustrates an exemplary procedure for returning a dateID to be inserted as a reference for a date. In accordance with this procedure, first, all records are selected where the de-identified date of the record falls within the range that could correspond to a desired date. For example, if the de-identification range allows for de-identified dates within fifteen days of the actual date, then all records in the lookup table having a de-identified date within fifteen days of the desired date would be selected. These records are inserted into a dummy table with the actual dates being decrypted. Next, the records where the decrypted actual date does not correspond to the desired date are deleted from the dummy table, thus leaving the dummy table populated with one or more records corresponding to the desired date. A dateID of one of these records corresponding to the desired date is randomly selected for use and returned.

FIG. 10 illustrates an exemplary procedure for returning the first and last dateIDs for a given date. Similar to the procedure illustrated in FIG. 9, in accordance with this procedure, first, all records are selected where the de-identified date of the record falls within the range that could correspond to a desired date. These records are inserted into a dummy table with the actual dates being decrypted. Next, the records where the decrypted actual date does not correspond to the desired date are deleted from the dummy table, thus leaving the dummy table populated with one or more records corresponding to the desired date. The lowest remaining dateID is the first dateID for the desired date, while the highest remaining dateID is the last dateID for the desired date.

It will be appreciated that such first and last dateID information can be utilized to quickly search for all records within a date range. For example, if a user wishes to search for all records between Dec. 24, 2012 and Jan. 1, 2013 (or filter out all records not falling within this span), a preferred methodology could involve simply ascertaining the first/lowest dateID for the start date of Dec. 24, 2012 (which might be, for example, 10237) and the last/highest dateID for the end date of Jan. 1, 2013 (which might be, for example, 14253), and then searching for all records having a dateID falling within this range.

Based on the foregoing description, it will be readily understood by those persons skilled in the art that the present invention is susceptible of broad utility and application. Many embodiments and adaptations of the present invention other than those specifically described herein, as well as many variations, modifications, and equivalent arrangements, will be apparent from or reasonably suggested by the present invention and the foregoing descriptions thereof, without departing from the substance or scope of the present invention. Accordingly, while the present invention has been described herein in detail in relation to one or more preferred embodiments, it is to be understood that this disclosure is only illustrative and exemplary of the present invention and is made merely for the purpose of providing a full and enabling disclosure of the invention. The foregoing disclosure is not intended to be construed to limit the present invention or otherwise exclude any such other embodiments, adaptations, variations, modifications or equivalent arrangements, the present invention being limited only by the claims appended hereto and the equivalents thereof.

What is claimed is:

1. A method executable on a computing device by instructions loaded in memory of the computing device for searching of data containing protected date information representing protected health information, the method comprising:
   (a) adding dateID and date values to a lookup table by,
      (i) for a start date, adding a first dateID and date value pair to the lookup table by
         (A) generating a first random number,
         (B) adding the generated first random number to a minimum value to establish a first ID value,
         (C) determining whether the established first ID value is unique, and incrementing the established first ID value if it is not until it is unique,
         (D) thereafter, once it is determined that the established first ID value is unique, inserting the established first ID value in association with the start date into the lookup table,
      (ii) for the start date, adding an additional number of dateID and date value pairs based on an indication of a desired number of dateIDs to be assigned to a date by repeatedly
         (A) generating a respective random number,
         (B) adding the generated respective random number to the established first ID value to establish a respective ID value,
         (C) determining whether the established respective ID value is unique, and incrementing the established respective ID value if it is not until it is unique,
         (D) thereafter, once it is determined that the established respective ID value is unique, inserting the established respective ID value in association with the start date into the lookup table;
      (iii) for each respective date between the start date and an end date, adding a number of dateID and date value pairs, the number being based on an indication of a desired number of dateIDs to be assigned to a date, by repeatedly
         (A) generating a respective random number,
         (B) adding the generated respective random number to the last established ID value to establish a current respective ID value,
         (C) determining whether the established current respective ID value is unique, and incrementing the established current respective ID value if it is not until it is unique,
         (D) thereafter, once it is determined that the established current respective ID value is unique, inserting the established current respective ID value in association with the respective date into the lookup table;
   (b) receiving, from a user via an input device, a query for records falling within a certain date range;
   (c) determining a minimum dateID value corresponding to a query start date associated with the certain date range by
      (i) inserting, into a first dummy table, records from the lookup table that have a de-identified date value falling within a certain number of days of the query start date,
      (ii) deleting, from the first dummy table, one or more records where a decrypted date value of the record does not correspond to the query start date, and
      (iii) determining a minimum dateID value of the remaining records;
   (d) determining a maximum dateID value corresponding to a query end date associated with the certain date range by
      (i) inserting, into a second dummy table, records from the lookup table that have a de-identified date value falling within a certain number of days of the query start date,
      (ii) deleting, from the second dummy table, one or more records where a decrypted date value of the record does not correspond to the query end date, and
      (iii) determining a maximum dateID value of the remaining records;
   (e) selecting, from a datasource containing records corresponding to patient encounters, all encounters having a dateID value falling within a range corresponding to the determined minimum and maximum dateID values;
   (f) presenting, to the user via a display device, an indication of one or more of the records selected from the datasource.

2. The method of claim 1, wherein the first dummy table and the second dummy table are the same dummy table.

3. The method of claim 1, wherein the first dummy table and the second dummy table are different dummy tables.

4. The method of claim 1, wherein the datasource comprises a database.

5. The method of claim 1, wherein the datasource comprises a data warehouse.

6. The method of claim 1, wherein the datasource comprises a database of a data warehouse.

7. The method of claim 1, wherein the method further includes generating a de-identified date for each dateID in the lookup table.

8. The method of claim 7, wherein the method further includes storing the generated de-identified date for each dateID in the lookup table in association with the respective dateID.

9. The method of claim 7, wherein each generated de-identified date is generated to be within a certain number of days of a date associated with the dateID the de-identified date is generated for.

10. The method of claim 9, wherein the certain number of days is fifteen days.

11. A method executable on a computing device by instructions loaded in memory of the computing device for searching of data containing protected date information representing protected health information utilizing a lookup table containing encrypted date values, dateID values, and de-identified date values, the method comprising:
   (a) receiving, from a user via an input device, a query for medical records having a date value falling within a certain date range;
   (b) determining a minimum dateID value corresponding to a query start date associated with the certain date range by
      (i) inserting, into a first dummy table, records from a lookup table that have a de-identified date value falling within a certain number of days of the query start date,
      (ii) deleting, from the first dummy table, one or more records where a decrypted date value of the record does not correspond to the query start date, and
      (iii) determining a minimum dateID value of the remaining records;
   (c) determining a maximum dateID value corresponding to a query end date associated with the certain date range by (i) inserting, into a second dummy table, records from the lookup table that have a de-identified date value falling within a certain number of days of the query start date,
(ii) deleting, from the second dummy table, one or more records where a decrypted date value of the record does not correspond to the query end date, and
(iii) determining a maximum dateID value of the remaining records;
(d) selecting, from a datasource containing records corresponding to patient encounters, all encounters having a dateID value falling within a range corresponding to the determined minimum and maximum dateID values;
(e) presenting, to the user via a display device, an indication of one or more of the records selected from the datasource.

12. The method of claim 11, wherein the query for medical records comprises a query for patient encounter records.

13. The method of claim 11, wherein the first dummy table and the second dummy table are the same dummy table.

14. The method of claim 11, wherein the first dummy table and the second dummy table are different dummy tables.

15. The method of claim 11, wherein the datasource comprises a database.

16. The method of claim 11, wherein the datasource comprises a data warehouse.

17. The method of claim 11, wherein the datasource comprises a database of a data warehouse.

18. The method of claim 11, wherein inserting, into a second dummy table, records from the lookup table that have a de-identified date value falling within a certain number of days of the query start date comprises inserting records that have a de-identified date value falling within fifteen days of the query start date.

19. The method of claim 11, wherein inserting, into a second dummy table, records from the lookup table that have a de-identified date value falling within a certain number of days of the query end date comprises inserting records that have a de-identified date value falling within fifteen days of the query end date.

* * * * *